US010674765B2

(12) United States Patent
Davis et al.

(10) Patent No.: US 10,674,765 B2
(45) Date of Patent: Jun. 9, 2020

(54) AEROSOL DELIVERY DEVICE WITH IMPROVED ATOMIZER

(71) Applicant: RAI Strategic Holdings, Inc., Winston-Salem, NC (US)

(72) Inventors: Michael F. Davis, Clemmons, NC (US); Noah Mark Minskoff, Palo Alto, CA (US); Stephen Benson Sears, Siler City, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 480 days.

(21) Appl. No.: 15/472,839

(22) Filed: Mar. 29, 2017

(65) Prior Publication Data

US 2018/0279672 A1 Oct. 4, 2018

(51) Int. Cl.

| | |
|---|---|
| ***A24F 47/00*** | (2020.01) |
| ***A61M 15/06*** | (2006.01) |
| ***A61M 11/04*** | (2006.01) |

(52) U.S. Cl.

CPC ......... *A24F 47/008* (2013.01); *A61M 11/042* (2014.02); *A61M 15/06* (2013.01); *A61M 2205/3653* (2013.01); *A61M 2205/8206* (2013.01)

(58) Field of Classification Search

CPC ... A24F 47/008; A61M 11/042; A61M 15/06; A61M 2205/3653; A61M 2205/8206

USPC .......................................................... 392/395

See application file for complete search history.

(56) References Cited

U.S. PATENT DOCUMENTS

| | | | |
|---|---|---|---|
| 2,057,353 | A | 10/1936 | Whittemore, Jr. |
| 2,104,266 | A | 1/1938 | McCormick |
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |
| 5,261,424 | A | 11/1993 | Sprinkel, Jr. |
| 5,388,574 | A | 2/1995 | Ingebrethsen et al. |
| 5,530,225 | A | 6/1996 | Hajaligol |
| 5,687,746 | A | 11/1997 | Rose et al. |
| 5,726,421 | A | 3/1998 | Fleischhauer et al. |
| 5,865,185 | A | 2/1999 | Collins et al. |
| 5,894,841 | A | 4/1999 | Voges |
| 6,125,853 | A | 10/2000 | Susa et al. |
| 6,155,268 | A | 12/2000 | Takeuchi |

(Continued)

FOREIGN PATENT DOCUMENTS

| | | |
|---|---|---|
| CN | 1541577 | 11/2004 |
| CN | 2719043 | 8/2005 |

(Continued)

*Primary Examiner* — Ibrahime A Abraham
*Assistant Examiner* — Biniam B Asmelash
(74) *Attorney, Agent, or Firm* — Womble Bond Dickinson (US) LLP

(57) ABSTRACT

The present disclosure relates to aerosol delivery devices, methods of forming such devices, and elements of such devices. In some embodiments, the present disclosure provides atomizers and elements thereof, such as a combined wick and heater configured to improve vaporization response time, particularly on porous, monolithic wicks. The wick can have a tapered end that engages the interior of a substantially basket-shaped wire heater coil. The heater also may be in the form of a conductive mesh that is present on a portion of the wick.

5 Claims, 6 Drawing Sheets

(56) References Cited

U.S. PATENT DOCUMENTS

| | | | |
|---|---|---|---|
| 7,117,867 B2 | 10/2006 | Cox et al. | |
| 7,832,410 B2 | 11/2010 | Hon | |
| 8,314,591 B2 | 11/2012 | Terry et al. | |
| 8,365,742 B2 | 2/2013 | Hon | |
| 8,499,766 B1 | 8/2013 | Newton | |
| 2005/0016550 A1 | 1/2005 | Katase | |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0188490 A1 | 7/2009 | Hon | |
| 2009/0272379 A1 | 11/2009 | Thorens et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0290248 A1 | 12/2011 | Schennum | |
| 2012/0111347 A1 | 5/2012 | Hon | |
| 2012/0260927 A1 | 10/2012 | Liu | |
| 2012/0279512 A1 | 11/2012 | Hon | |
| 2013/0037041 A1 | 2/2013 | Worm et al. | |
| 2013/0056013 A1 | 3/2013 | Terry et al. | |
| 2013/0306084 A1 | 11/2013 | Flick | |
| 2014/0000638 A1 | 1/2014 | Sebastian et al. | |
| 2014/0060554 A1 | 3/2014 | Collett et al. | |
| 2014/0060555 A1 | 3/2014 | Chang et al. | |
| 2014/0096781 A1* | 4/2014 | Sears | A24F 47/008 131/328 |
| 2014/0096782 A1 | 4/2014 | Ampolini et al. | |
| 2014/0123989 A1* | 5/2014 | LaMothe | A24F 47/008 131/328 |
| 2014/0209105 A1 | 7/2014 | Sears et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2016/0007652 A1* | 1/2016 | Taluskie | A24F 47/008 131/328 |

FOREIGN PATENT DOCUMENTS

| | | |
|---|---|---|
| CN | 201379072 | 1/2010 |
| EP | 0 295 122 | 12/1988 |
| EP | 0 845 220 | 6/1998 |
| EP | 1 618 803 | 1/2006 |
| GB | 2469850 | 11/2010 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | WO 2016/001921 | 1/2016 |

* cited by examiner

AEROSOL DELIVERY DEVICE WITH IMPROVED ATOMIZER

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference.

It would be desirable to provide a vapor-forming unit of an aerosol delivery device, the vapor-forming unit being configured for improved vapor formation and/or improved integration with a power unit. It would also be desirable to provide aerosol delivery devices that are prepared utilizing such vapor-forming units.

SUMMARY OF THE DISCLOSURE

The present disclosure relates to aerosol delivery devices, methods of forming such devices, and elements of such devices. The aerosol delivery devices can particularly integrate ceramic wicks to form vapor-forming units that can be combined with power units to form the aerosol delivery devices.

In one or more embodiments, the present disclosure can relate to an atomizer that is particularly useful in an aerosol delivery device. The atomizer particularly can include at least a fluid transport element and a heater. The fluid transport element can be formed of a rigid material and particularly can be a porous monolith, such as a porous ceramic or porous glass. The combined heater and fluid transport element can exhibit improved vapor formation in light of certain configurations of the individual materials.

In some embodiments, an exemplary atomizer can comprise: a fluid transport element in the form of a rigid, porous monolith, the fluid transport element having a first end that is tapered and having a second end; and a heater in a substantially conical configuration and including an interior area that receives and substantially matches the tapered first end of the fluid transport element. In further embodiments, such atomizer may be defined in relation to one or more of the following statements, which may be combined in any number and order.

The rigid, porous monolith can be formed of porous ceramic or porous glass.

The fluid transport element can exclude any fibrous material.

The fluid transport element can have a main body with a longitudinal length extending between the tapered first end and the second end, the main body having a diameter that is substantially constant along the longitudinal length thereof.

The tapered first end of the fluid transport element can form about 5% to about 50% of a total length of the fluid transport element.

The tapered first end can taper (i.e., gradually decrease) from a first diameter that is approximately the same as the diameter of the main body to a second diameter that is about 50% or less of the diameter of the main body of the fluid transport element.

The atomizer can be defined by the following: the heater can have an upper end with a diameter that is substantially the same as the diameter of the main body of the fluid transport element; the heater can have a height that is substantially the same as a length of the tapered first end of the fluid transport element; the heater can have a lower end with a diameter that is about 50% or less of the diameter of the upper end of the heater.

The present disclosure also can relate to an atomizer comprising: a fluid transport element in the form of a rigid, porous monolith, the fluid transport element having a first end and a second end; and a heater contacting at least a portion of an outer surface of the fluid transport element, the heater being in the form of a conductive mesh. In further embodiments, such atomizer may be defined in relation to one or more of the following statements, which may be combined in any number and order.

The conductive mesh can be formed from a plurality of crossing, conductive filaments.

The conductive mesh can have a regular pattern of conductive filaments forming parallelograms (or other geometric shapes) surrounding insulating spaces.

The insulating spaces can be open or can be at least partially filled.

The insulating spaces can have an average individual area of about 0.01 μm to about 0.5 μm.

The fluid transport element can have an overall longitudinal length, and the conductive mesh can be present on about 10% to about 80% of the overall longitudinal length of the fluid transport element.

The conductive mesh can be present on about 30% to about 70% of the overall longitudinal length of the fluid transport element.

In one or more embodiments, the present disclosure specifically can relate to an aerosol delivery device comprising an atomizer as otherwise described herein. In particular, such aerosol delivery device can comprise a reservoir including an aerosol precursor composition, and the second end of the fluid transport element from the atomizer can extend into the reservoir so as to be in contact with the aerosol precursor composition. The fluid transport element can wick or otherwise transport aerosol precursor composition from the reservoir to the heater that is in thermal connection with the fluid transport element (the heater having any configuration as otherwise described herein). The heater is positioned exterior to the reservoir so as to vaporize at least a portion of the aerosol precursor composition that is transported from the reservoir via the fluid transport element. The formed vapor can combine with air that is drawn into the aerosol delivery device to form an aerosol that flows to a mouthend of the aerosol delivery device and exits the aerosol delivery device. The aerosol delivery device including the atomizer can be a single, unitary structure housing all elements as described herein useful for forming an aerosol (e.g., power, control, and vaporization elements). The aerosol delivery device can be a cartridge or tank that does not include any power element (e.g., does not include a battery) and/or does not include a control element (e.g., does not include a printed circuit board with a sensor or other electronic controller thereon).

BRIEF DESCRIPTION OF THE FIGURES

Figure 1:
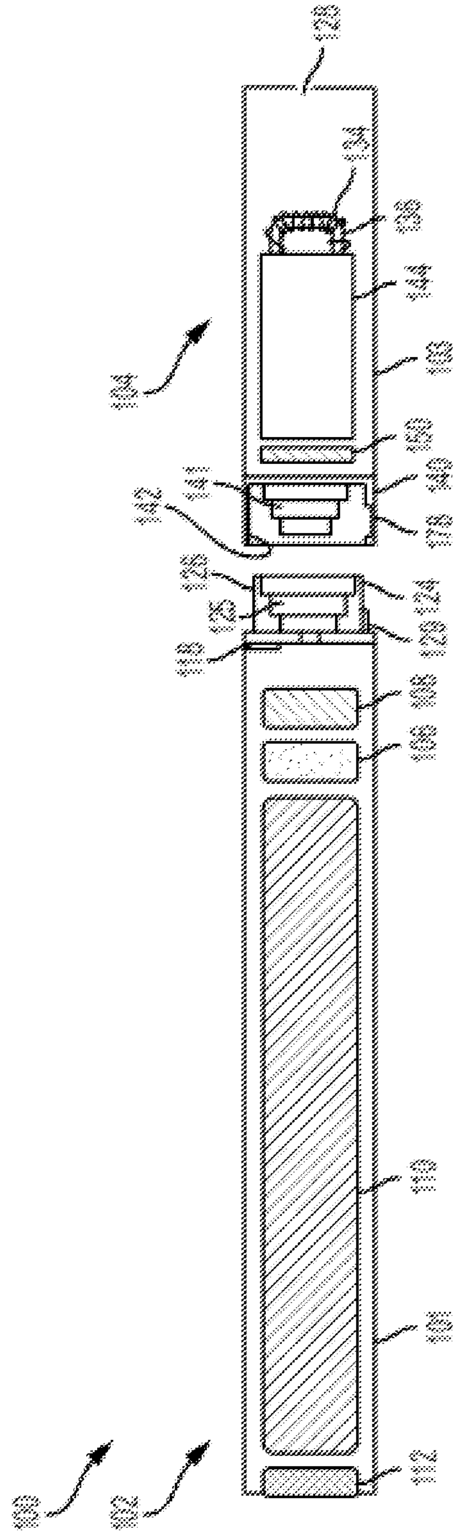
Figure 2A:
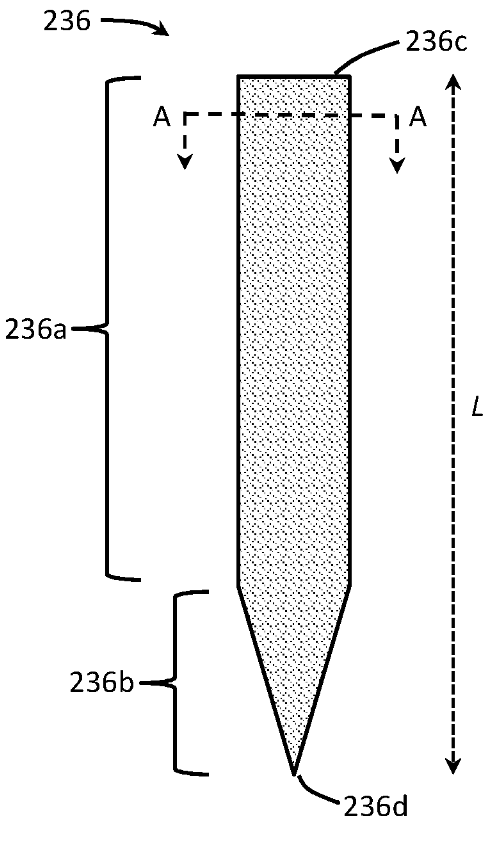
Figure 2B:
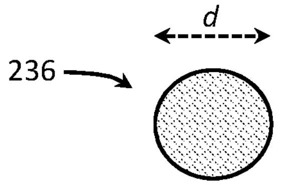
Figure 3:
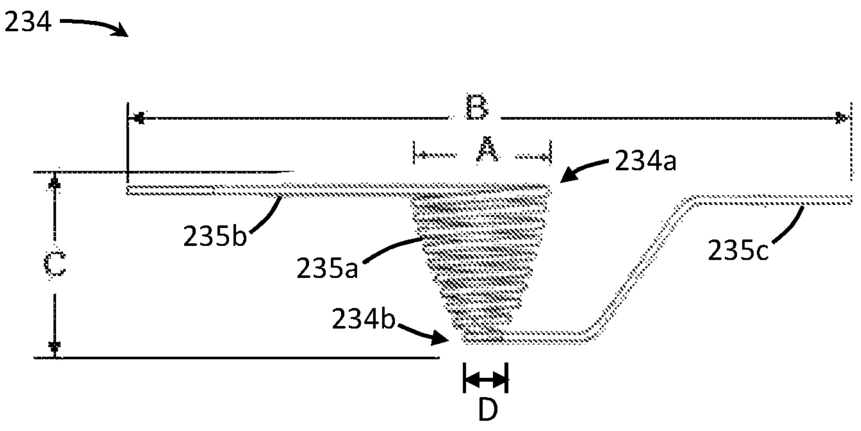
Figure 4:
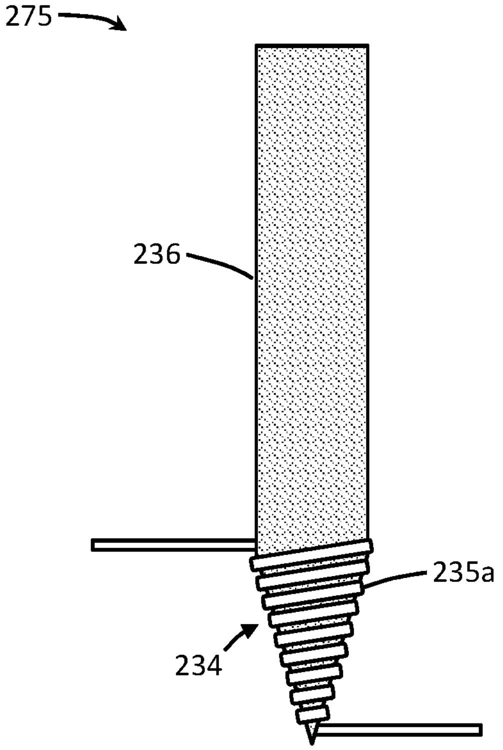
Figure 5:
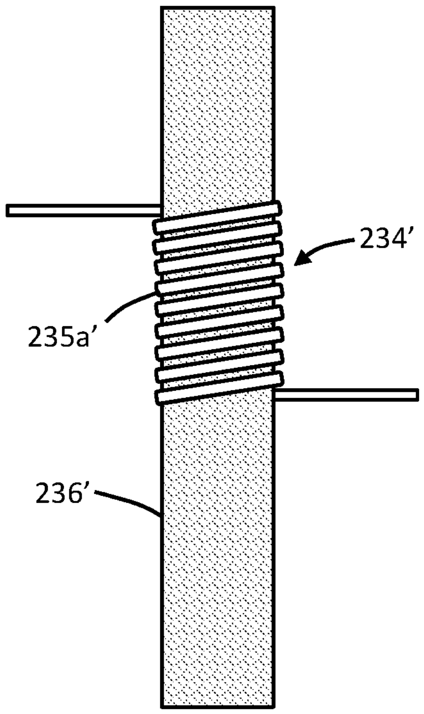
Figure 6:
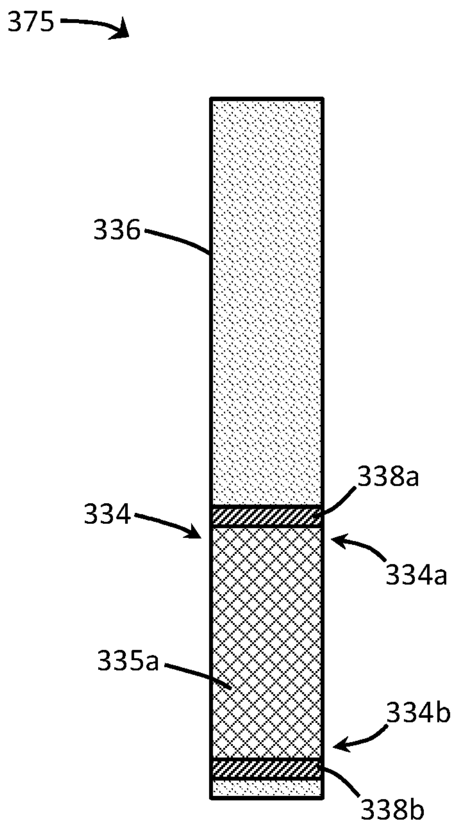
Figure 7:
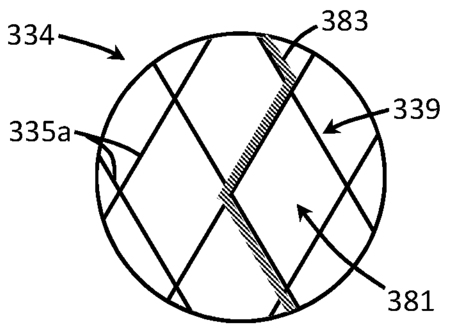
Figure 8:
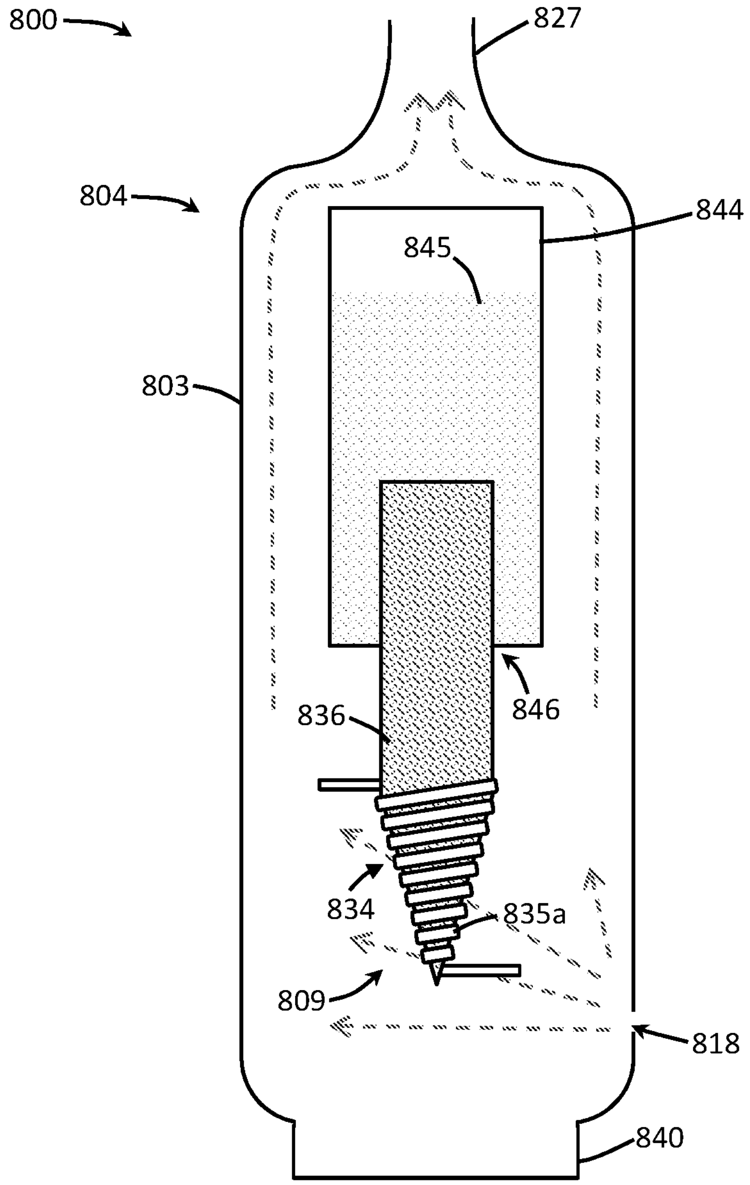

Having thus described the disclosure in the foregoing general terms, reference will now be made to the accompanying drawings, which are not necessarily drawn to scale, and wherein:

FIG. 1 is a partially cut-away view of an aerosol delivery device comprising a cartridge and a power unit including a variety of elements that may be utilized in an aerosol delivery device according to various embodiments of the present disclosure;

FIG. 2A is an illustration of a fluid transport element according to various embodiments of the present disclosure that includes a tapered end;

FIG. 2B is a cross-sectional view of the fluid transport element from FIG. 2A through line A-A showing the cross-sectional shape thereof;

FIG. 3 is an illustration of a heater according to various embodiments of the present disclosure, the heater having a substantially conical shape wherein a diameter of an upper end of the heater is greater than a diameter of a lower end of the heater;

FIG. 4 is an illustration of an atomizer according to various embodiments of the present disclosure, the atomizer including a fluid transport element with a tapered end and including a heater having a substantially conical shape, the heater engaging the tapered end of the fluid transport element;

FIG. 5 is an illustration of a comparative atomizer having a single stranded heating wire wrapped around a substantially central section of a fluid transport element that has a substantially constant diameter along the full length thereof;

FIG. 6 is an illustration of an atomizer according to various embodiments of the present disclosure, the atomizer including a fluid transport element and including a conductive mesh heater surrounding a portion of the fluid transport element;

FIG. 7 is an enlarged view of a section of a conductive mesh heater according to various embodiments of the present disclosure; and FIG. 8 is a partially cut-away view of an aerosol delivery device comprising a tank that includes a reservoir and an atomizer according to various embodiments of the present disclosure.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one embodiment, all of the components of the aerosol delivery device are contained within one housing. Alternatively, an aerosol delivery device can comprise two or more housings that are joined and are separable. For example, an aerosol delivery device can possess at one end a control body (or power unit) comprising a housing containing one or more components (e.g., a battery and various electronics for controlling the operation of that article), and at the other end and removably attached thereto an outer body or shell containing aerosol forming components (e.g., one or more aerosol precursor components, such as flavors and aerosol formers, one or more heaters, and/or one or more wicks).

Aerosol delivery devices of the present disclosure can be formed of an outer housing or shell that is not substantially tubular in shape but may be formed to substantially greater dimensions. The housing or shell can be configured to include a mouthpiece and/or may be configured to receive a separate shell (e.g., a cartridge or tank) that can include consumable elements, such as a liquid aerosol former, and can include a vaporizer or atomizer.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in the background art section of the present disclosure.

One example embodiment of an aerosol delivery device 100 illustrating components that may be utilized in an aerosol delivery device according to the present disclosure is provided in FIG. 1. As seen in the cut-away view illustrated therein, the aerosol delivery device 100 can comprise a power unit 102 and a cartridge 104 that can be permanently or detachably aligned in a functioning relationship. Engagement of the power unit 102 and the cartridge 104 can be press fit (as illustrated), threaded, interference fit, magnetic, or the like. In particular, connection components, such as further described herein may be used. For example, the power unit may include a coupler that is adapted to engage a connector on the cartridge.

In specific embodiments, one or both of the power unit 102 and the cartridge 104 may be referred to as being disposable or as being reusable. For example, the power unit may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a power unit connector at an opposing end is disclosed in U.S. Pat. Pub. No. 2014/0261495 to Novak et al., which is incorporated herein by reference. Further, in some embodiments the cartridge may comprise a single-use cartridge, as disclosed in U.S. Pat. No. 8,910,639 to Chang et al., which is incorporated herein by reference.

As illustrated in FIG. 1, a power unit 102 can be formed of a power unit shell 101 that can include a control component 106 (e.g., a printed circuit board (PCB), an integrated circuit, a memory component, a microcontroller, or the like), a flow sensor 108, a battery 110, and an LED 112, and such components can be variably aligned. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference. It is understood that not all of the illustrated elements are required. For example, an LED may be absent or may be replaced with a different indicator, such as a vibrating indicator. Likewise, a flow sensor may be replaced with a manual actuator, such as a push button.

A cartridge 104 can be formed of a cartridge shell 103 enclosing the reservoir 144 that is in fluid communication with a liquid transport element 136 adapted to wick or otherwise transport an aerosol precursor composition stored in the reservoir housing to a heater 134. A liquid transport element can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus can be any material that contains an open pore network (i.e., a plurality of pores that are interconnected so that fluid may flow from one pore to another in a plurality of direction through the element). As further discussed herein, some embodiments of the present disclosure can particularly relate to the use of non-fibrous transport elements. As such, fibrous transport elements can be expressly excluded. Alternatively, combinations of fibrous transport elements and non-fibrous transport elements may be utilized. Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics).

An opening 128 may be present in the cartridge shell 103 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 150, which may include an integrated circuit, a memory component, a sensor, or the like. The electronic component 150 may be adapted to communicate with the control component 106 and/or with an external device by wired or wireless means. The electronic component 150 may be positioned anywhere within the cartridge 104 or its base 140.

Although the control component 106 and the flow sensor 108 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the power unit. In some embodiments, the air flow sensor may comprise its own circuit board or other base element to which it can be attached. In some embodiments, a flexible circuit board may be utilized. A flexible circuit board may be configured into a variety of shapes, include substantially tubular shapes. Configurations of a printed circuit board and a pressure sensor, for example, are described in U.S. Pat. Pub. No. 2015/0245658 to Worm et al., the disclosure of which is incorporated herein by reference.

The power unit 102 and the cartridge 104 may include components adapted to facilitate a fluid engagement therebetween. As illustrated in FIG. 1, the power unit 102 can include a coupler 124 having a cavity 125 therein. The cartridge 104 can include a base 140 adapted to engage the coupler 124 and can include a projection 141 adapted to fit within the cavity 125. Such engagement can facilitate a stable connection between the power unit 102 and the cartridge 104 as well as establish an electrical connection between the battery 110 and control component 106 in the power unit and the heater 134 in the cartridge. Further, the power unit shell 101 can include an air intake 118, which may be a notch in the shell where it connects to the coupler 124 that allows for passage of ambient air around the coupler and into the shell where it then passes through the cavity 125 of the coupler and into the cartridge through the projection 141.

A coupler and a base useful according to the present disclosure are described in U.S. Pat. Pub. No. 2014/0261495 to Novak et al., the disclosure of which is incorporated herein by reference. For example, a coupler as seen in FIG. 1 may define an outer periphery 126 configured to mate with an inner periphery 142 of the base 140. In one embodiment the inner periphery of the base may define a radius that is substantially equal to, or slightly greater than, a radius of the outer periphery of the coupler. Further, the coupler 124 may define one or more protrusions 129 at the outer periphery 126 configured to engage one or more recesses 178 defined at the inner periphery of the base. However, various other embodiments of structures, shapes, and components may be employed to couple the base to the coupler. In some embodiments the connection between the base 140 of the cartridge 104 and the coupler 124 of the power unit 102 may be substantially permanent, whereas in other embodiments the connection therebetween may be releasable such that, for example, the power unit may be reused with one or more additional cartridges that may be disposable and/or refillable.

The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, multifaceted shapes, or the like. In particular, the power unit 102 may be non-rod-like and may rather be substantially rectangular, round, or have some further shape. Likewise, the power unit 102 may be substantially larger than a power unit that would be expected to be substantially the size of a conventional cigarette.

The reservoir 144 illustrated in FIG. 1 can be a container (e.g., formed of walls substantially impermeable to the aerosol precursor composition) or can be a fibrous reservoir. Container walls can be flexible and can be collapsible. Container walls alternatively can be substantially rigid. A container preferably is substantially sealed to prevent passage of aerosol precursor composition therefrom except via any specific opening provided expressly for passage of the aerosol precursor composition, such as through a transport element as otherwise described herein. In exemplary embodiments, the reservoir 144 can comprise one or more layers of nonwoven fibers substantially formed into the shape of a tube encircling the interior of the cartridge shell 103. An aerosol precursor composition can be retained in the reservoir 144. Liquid components, for example, can be sorptively retained by the reservoir 144 (i.e., when the reservoir 144 includes a fibrous material). The reservoir 144 can be in fluid connection with a liquid transport element 136. The liquid transport element 136 can transport the aerosol precursor composition stored in the reservoir 144 via capillary action to the heating element 134 that is in the form of a metal wire coil in this embodiment. As such, the heating element 134 is in a heating arrangement with the liquid transport element 136.

In use, when a user draws on the article 100, airflow is detected by the sensor 108, the heating element 134 is activated, and the components for the aerosol precursor composition are vaporized by the heating element 134. Drawing upon the mouthend of the article 100 causes ambient air to enter the air intake 118 and pass through the cavity 125 in the coupler 124 and the central opening in the projection 141 of the base 140. In the cartridge 104, the drawn air combines with the formed vapor to form an aerosol. The aerosol is whisked, aspirated, or otherwise drawn away from the heating element 134 and out the mouth opening 128 in the mouthend of the article 100. Alternatively, in the absence of an airflow sensor, the heating element 134 may be activated manually, such as by a push button.

An input element may be included with the aerosol delivery device (and may replace or supplement an airflow or pressure sensor). The input may be included to allow a user to control functions of the device and/or for output of information to a user. Any component or combination of components may be utilized as an input for controlling the function of the device. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference.

In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference.

The aerosol delivery device can incorporate a sensor or detector for control of supply of electric power to the heat generation element when aerosol generation is desired (e.g., upon draw during use). As such, for example, there is provided a manner or method for turning off the power supply to the heat generation element when the aerosol delivery device is not be drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference.

The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pub. No. 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 1 ml or more, about 2 ml or more, about 5 ml or more, or about 10 ml or more of the aerosol precursor composition may be included.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article illustrated in FIG. 1 or as otherwise described above may be included in an aerosol delivery device according to the present disclosure.

In one or more embodiments, the present disclosure particularly can relate to aerosol delivery devices that are configured to provide increased vapor production. Such increase can arise from a variety of factors. In some embodiments, a liquid transport element (i.e., a wick or wicking element) can be formed partially or completely from a porous monolith, such as a porous ceramic, a porous glass, or the like. Exemplary monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference. The porous monolith can form a substantially solid wick. In particular, the transport element can be substantially a single, monolithic material rather than a bundle of individual fibers as known in the art.

The use of a rigid, porous monolith as a fluid transport element is beneficial for improving uniformity of heating and reducing possible charring of the fluid transport element when non-uniform heating occurs. It can also be desirable to eliminate the presence of any fibrous materials in an aerosol delivery device. Despite such benefits, porous monoliths also present certain challenges for successful implementation as a fluid transport element. Such challenges are in part due to the different material properties of porous monoliths (e.g., porous ceramics) compared to fibrous wicks. For example, alumina has both a higher thermal conductivity and a higher heat capacity than silica. These thermal properties cause heat to be drawn away from the aerosol precursor composition at the interface of the wick and the heater, and this can require a higher initial energy output to achieve comparable fluid vaporization. The present disclosure realizes means for overcoming such difficulties.

In some embodiments utilizing a porous monolith, energy requirements for vaporization when using a porous monolith can be minimized, and vaporization response time can be improved by increasing heat flux density (measured in Watts per square meter—$W/m^2$) over the surface of the porous monolith fluid transport element. The present disclosure particularly describes embodiments suitable to provide such increase in heat flux density.

In one or more embodiments, the present disclosure than can relate to an atomizer configuration wherein a porous monolithic fluid transport element has a specifically shaped portion that is combined with a heater having a substantially matching shape. For example, a fluid transport element 236 is shown in FIG. 2A and is in the form of a substantially rigid, porous monolith. As seen in FIG. 2B, the fluid transport element has a substantially round cross section, but other cross sectional geometries are also encompassed. The fluid transport element 236 has a main body 236*a*, a first end that is tapered 236*b*, and a second end 236*c*. While the fluid transport element 236 is illustrated as being substantially straight, other configurations are also encompassed, such having one or more bends or being curved. The main body 236*a* of the fluid transport element 236 has a diameter d that is substantially constant along the longitudinal length of the main body 236*a*. The second end 236*c* can have a diameter that is substantially the same as the diameter d of the main body 236*a*; however, the diameter of the second end 236*c* can be lesser or greater than the diameter d of the main body 236*a*. As illustrated, the tapered end 236*b* of the transport element 236 forms approximately 25% of the total length L of the transport element. In various embodiments, the tapered end 236*b* forms about 5% to about 50%, about 10% to about 40%, or about 15% to about 35% of the total length L of the transport element 236. The tapered end 236*b* of the transport element 236 is configured so as to start with a diameter that is approximately the same as the diameter d of the main body 236*a* and then gradually decrease to a point 236*d*. Although the point 236*d* is illustrated as a sharp point, such configuration is not required. Preferably, the point 236*d* has a diameter that is about 50% or less, about 35% or less, about 20% or less, or about 10% or less of the diameter d of the main body 236*a*, with an exemplary lower range of about 5% or about 1% of the diameter d of the main body. In some embodiments, the point 236*d* can be substantially rounded or flattened.

A heater 234 is shown in FIG. 3, and the heater is formed of a heating wire 235*a* that is shaped to substantially match the tapered end 236*b* of the transport element 236. As illustrated, the heater 234 is substantially basket shaped. In order to substantially match the tapered end 236*b* of the transport element 236, the heater 234 can have dimensions that are substantially similar to dimensions of the transport element 236. In an exemplary embodiment, the heater 234 has an upper end 234*a* with a diameter A that is substantially the same as the diameter d of the main body 236*a* of the transport element 236. Substantially the same indicates that the diameter A of the upper end 234*a* of the heater 234 is ±10% of the diameter d of the main body 236*a* of the transport element 236. The heater 234 also has a height C that is substantially the same as the length of the tapered end 236*b* of the transport element 236. Substantially the same indicates that the height C of the heater 234 is ±10% of the length of the tapered end 236*b* of the transport element 236. In some embodiments, the height C of the heater 234 is no greater than the length of the tapered end 236*b* of the transport element 236. For example, the height C of the heater 234 can be about 50% to about 100%, about 60% to about 99%, or about 65% to about 98% of the length of the tapered end 236*b* of the transport element 236. The heater 234 also can have a lower end 234*b* with a diameter D that is less than the diameter A of the upper end 234*a* of the heater. The diameter D of the lower end 234*b* of the heater 234 preferably is about 50% or less, about 35% or less, about 20% or less, or about 10% or less of the diameter A of the upper end 234*a* of the heater. For example, diameter D can be about 1% to about 50%, about 2% to about 40%, or about 5% to about 30% of diameter A. The diameter of the heater 234 can gradually decrease from diameter A at the upper end 234*a* of the heater to diameter D at the lower end 234*b* of the heater. The heater 234 has an open interior area that is configured to receive the tapered end 236*b* of the transport element 236.

The heater 234 can further include electrical leads (235*b*, 235*c*) to provide positive and negative electrical connections for the heater. The electrical leads (235*b*, 235*c*) can be integrally formed with the heating wire 235*a* or can be separate elements that can be attached (e.g., by welding or using a connector) to the heating wire. The heater 234 can have an overall width B that can include the overall width of the coil formed by the heating wire 235*a* and the length of the electrical leads (235*b*, 235*c*).

The combination of the transport element 236 and the heater 234 is shown in FIG. 4. As seen therein, an atomizer 275 is formed of a transport element 236 in the form of a rigid, porous monolith and a heater 234 wrapped around a tapered end of the transport element. The heater 234 comprises nine coils of the heater wire 235*a*. As seen, the heater 234 is in a substantially conical configuration and includes an interior area that receives and substantially matches the tapered end of the fluid transport element. In this configuration, energy from the heater 234 is focused into the smaller surface area of the tapered end of the wick. By comparison, as illustrated in FIG. 5, a heater 234' formed of nine coils of heater wire 235*a*' wrapped around a constant diameter portion of a fluid transport element 236' covers a significantly larger surface area of the fluid transport element and thus causes the energy to be less focused. In such comparative atomizer, heat flux density is significantly less than when the heater wire is coiled over a smaller surface area, as shown in FIG. 4.

In one or more embodiments, increased heat flux density and, thus, improved heating and vapor formation, may be achieved using an alternate heater configuration. For example, as illustrated in FIG. 6, a mesh or screen heater 334 may be used and can be effective to increase heater surface area coverage over a porous monolithic fluid transport element 336. The heater preferably is configured for contacting at least a portion of an outer surface of a fluid transport element, the heater being in the form of a conductive mesh. As used herein, the terms mesh and screen are meant to be interchangeable and to specifically refer to a network of intercrossing, conductive filaments 335*a*. As such, the conductive mesh can be considered to be network of conductive filaments and/or an interlaced structure. The conductive filaments 335*a* can be formed of any suitable, electrically conductive material, such as otherwise listed herein for formation of a heater. In one or more embodiments, the conductive filaments 335*a* can be at least partially interwoven with non-conductive filaments 383 or similar mater, which can be effective to improve direction of the flow of electrical current between the clasps 338*a* and 338*b*.

The conductive mesh heater 334 can circumferentially surround at least a portion of an outer surface of the fluid transport element 336. In some embodiments, the conductive mesh heater 334 may only partially surround at least a portion of an outer surface of the fluid transport element 336. The conductive mesh heater 334 can include a first end 334*a* and a second end 334*b* whereat coverage of the conductive mesh heater over the outer surface of the fluid transport element 336 terminates. The first end 334*a* and second end 334*b* of the conductive mesh heater 334 can include respective first and second clasps 338*a* and 338*b* that can secure the conductive mesh heater to the fluid transport element and/or can function as electrical connections between the conductive mesh heater and a power source.

As seen in FIG. 7, the conductive mesh heater 334 can comprise a plurality of crossing, conductive filaments 335*a*. The conductive mesh heater 334 can define a regular patter of conductive filaments 335*a* forming parallelograms 339 or other shapes consistent with a mesh configuration. The conductive filaments 335*a* particularly can surround insulating spaces 381. The insulating spaces 381 may be open (e.g., insulated by air) or may be at least partially filled with an insulator. The insulating spaces 381 can be configured to have a defined area so that the heating ability of the conductive mesh heater 334 is maximized for a minimized amount of power delivery to the conductive mesh heater. In some embodiments, the insulating spaces can have an average individual area of about 0.01 $\mu m^2$ to about 2 $mm^2$. In further embodiments, the insulating spaces can have an average individual area of about 0.05 $\mu m^2$ to about 1.5 $mm^2$, about 0.1 $\mu m^2$ to about 1 $mm^2$, about 0.25 $\mu m^2$ to about 0.5 $mm^2$, or about 0.5 $\mu m^2$ to about 0.1 $mm^2$. In some embodiments, the insulating spaces can have an average individual area in an upper range, such as about 0.005 $mm^2$ to about 2 $mm^2$, about 0.01 $mm^2$ to about 1.5 $mm^2$, or about 0.02 $mm^2$ to about 1 $mm^2$. In some embodiments, the insulating spaces can have an average individual area in a lower range, such as about 0.01 $\mu m^2$ to about 10 $\mu m^2$, about 0.02 $\mu m^2$ to about 5 $\mu m^2$, or about 0.05 $\mu m^2$ to about 1 $\mu m^2$.

Returning to FIG. 6, the conductive mesh heater 334, as illustrated, covers approximately 30% of the overall longitudinal length of the fluid transport element 336. In further embodiments, the conductive mesh heater 334 can be present on about 10% to about 80%, about 15% to about 75%, or about 20% to about 70% of the overall longitudinal length of the fluid transport element 336. The conductive mesh heater 334 may be positioned substantially proximate one end of the fluid transport element 336, or the conductive mesh heater may be positioned substantially centrally along the longitudinal length of the fluid transport element.

In further embodiments, an atomizer (275, 375) such as illustrated in FIG. 4 and/or FIG. 6 may be included in an aerosol delivery device (100) such as illustrated in FIG. 1. As such, any of the relevant elements from the aerosol delivery device 100 of FIG. 1 may be included in such aerosol delivery device including an atomizer (275 and/or 375) as described herein. As an exemplary embodiment, an aerosol delivery device 800 is illustrated in FIG. 8. The aerosol delivery device 800 includes a tank (or cartridge) 804 defined by an outer body or shell 803. The tank 804 includes a reservoir 844 that is at least partially filled with an aerosol precursor composition 845. The reservoir 844 is particularly configured as a closed body with a single aperture 846 configured to sealingly engage the porous monolithic fluid transport element 836. As such, the fluid transport element 836 extends or projects into the reservoir 844 so as to be in fluid communication or other contact with the aerosol precursor composition 845 and transport the aerosol precursor composition to the heater 834. When the heater 834 is activated, the aerosol precursor composition is vaporized to at least partially fill a vaporization zone 809 within the tank 804. Air drawn through air intake 818 whisks the formed vapor (e.g., in the form of an aerosol wherein the formed vapor is mixed with the air) from the vaporization zone 809 to the mouthpiece 827. As illustrated, the reservoir 844 is substantially centrally located in the tank 804, and the aerosol passes around the reservoir; however, other configurations of the elements are also encompassed. The tank 804 includes a connector 840 for connecting the tank to a control body or power unit (e.g., element 102 in FIG. 1). The connector 840 may have a similar structure as the base 140 illustrated in FIG. 1 or may have any further structure suitable for connecting the tank 804 to a control body/power unit. Although not illustrated, it is understood that electrical connections are included to provide an electrical connection between the heater 834 and a battery (e.g., element 110 in FIG. 1) or other power delivery device. An atomizer 375 illustrated in FIG. 6 may be used in addition or in the alternative to the combined heater 834 and fluid transport element 836 illustrated in FIG. 8.

A heater described herein generally may be positioned about an exterior portion of the fluid transport element. In one or more embodiments, however, a heater may be positioned at least partially internal to the fluid transport element. For example, a ceramic fluid transport element may be formed in the presence of a heater so that the ceramic fluid transport element and the heater are monolithic. In such embodiments, at least a sufficient amount of the heater suitable for forming an electrical contact will be positioned external to the fluid transport element. In some embodiments, a fluid transport element may be at least partially hollow—i.e., including an open space in which a heater may be positioned. In this manner, heating may proceed from the inside to the outside so that maximal vapor production is formed outwardly from the fluid transport element. If desired, a heater as described herein may be positioned at least partially internal to the fluid transport element. In some embodiments, a heater as described herein may be positioned on an outside surface of the fluid transport element, and a second heater may be positioned at least partially internal to the fluid transport element as noted above.

The use of at least two, separate heaters can be beneficial to improve vapor production. Specifically, a first heater can be used to pre-heat the liquid for vaporization within the liquid transport element, and a second heater can be used to actually vaporize the liquid. The pre-heating can reduce the total power and/or the absolute temperature and/or the duration of heating required to provide a desired volume of vapor. An internal heater, for example, may be a pre-heater, and an external heater may be a vaporizing heater. Alternatively, at least two separate heaters may be positioned on an external surface of the liquid transport element. One of the heaters may function as a pre-heater, and the other of the heaters may function as a vaporizing heater. For example, as illustrated in FIG. 8, a pre-heater (not illustrated) may be positioned between heater 834 (which may function as a vaporizing heater) and the reservoir 844. The pre-heater may pre-heat liquid aerosol precursor composition 845 flowing from the reservoir 844 to the vaporizing heater 834 so that the vaporizing heater may achieve vaporization more easily, as described above, and/or the pre-heater may reduce a viscosity of the liquid aerosol precursor composition to improve flow of the liquid from the reservoir to the vaporizing heater. A similar combination of heaters may be applied to the liquid transport element 336 in FIG. 6. In FIG. 8, the second heater positioned between heater 834 and the reservoir 844 may be a mesh heater as described herein, may be a simple wire coil, or may be any other type of heater useful for providing pre-heating to the liquid in the liquid transport element. In FIG. 6, the second heater on the liquid transport element 336 may be a further mesh heater, may be a simple wire coil, or may be any other type of heater useful for providing pre-heating to the liquid in the liquid transport element. For example, a heater coil 234' as illustrated in FIG. 5 may be added as a second heater in combination with a wire mesh heater (see FIG. 6) or a basket-shaped heater (see FIG. 4) as described herein.

In one or more instances, values described herein may be characterized with the word "about." It is understood that a value being "about" the stated amount indicates that the stated amount may be exactly the value indicated or may vary from the value indicated by up to 5%, up to 2%, or up to 1%.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An atomizer comprising:

a fluid transport element in a form of a rigid, porous monolith, the fluid transport element having a first end that is tapered and having a second end;

a heater in a conical configuration and including an interior area that receives and matches the tapered first end of the fluid transport element, wherein the fluid transport element has a main body with a longitudinal length extending between the tapered first end and the second end, the main body having a diameter that is constant along the longitudinal length thereof, the tapered first end forming 5% to 50% of the total length of the fluid transport element, the tapered first end tapering from a first diameter that is the same as the diameter of the main body to a second diameter that is 50% or less of the diameter of the main body of the fluid transport element, and wherein each of the following conditions is met:

the heater has an upper end with a diameter that is the same as the diameter of the main body of the fluid transport element;

the heater has a height that is the same as a length of the tapered first end of the fluid transport element;

the heater has a lower end with a diameter that is 50% or less of the diameter of the upper end of the heater.

2. The atomizer of claim 1, wherein the rigid, porous monolith is formed of porous ceramic or porous glass.

3. The atomizer of claim 1, wherein the fluid transport element excludes any fibrous material.

4. An aerosol delivery device comprising an atomizer according to claim 1.

5. The aerosol delivery device of claim 4, comprising a reservoir including an aerosol precursor composition, wherein the second end of the fluid transport element extends into the reservoir so as to be in contact with the aerosol precursor composition.

* * * * *